US006497987B1

(12) United States Patent
Kim et al.

(10) Patent No.: US 6,497,987 B1
(45) Date of Patent: Dec. 24, 2002

(54) PHOTOSENSITIVE LITHOCHOLATE DERIVATIVE AND CHEMICALLY AMPLIFIED PHOTORESIST COMPOSITION CONTAINING THE SAME

(75) Inventors: Hyun-woo Kim, Seongnam (KR); Sook Lee, Seoul (KR); Sang-gyun Woo, Suwon (KR)

(73) Assignee: Samsung Electronics Co., Ltd., Suwon (KR)

( * ) Notice: Subject to any disclaimer, the term of this patent is extended or adjusted under 35 U.S.C. 154(b) by 67 days.

(21) Appl. No.: 09/662,653

(22) Filed: Sep. 14, 2000

(30) Foreign Application Priority Data

Sep. 14, 1999 (KR) ............................................. 99-39337

(51) Int. Cl.⁷ ........................... G03C 1/73; G03F 7/004; C07J 1/00
(52) U.S. Cl. .................... 430/270.1; 430/914; 552/552; 552/555
(58) Field of Search ................................ 552/552, 555; 430/270.1, 914

(56) References Cited

U.S. PATENT DOCUMENTS 5,559,258 A * 9/1996 Enhsen et al. .............. 552/550

OTHER PUBLICATIONS

Gouin et al *Synthesis of 3α– and 3β–Dimers from Selected Bile Acids,* Steroids (1996) vol. 61, Issue 11, p. 664–669.*

\* cited by examiner

*Primary Examiner*—Janet Baxter
*Assistant Examiner*—Sin J. Lee
(74) *Attorney, Agent, or Firm*—Volentine Francos, PLLC

(57) ABSTRACT

A photosensitive compound, and a chemically amplified photoresist composition containing the photosensitive compound, maintain transparency even when exposed to a short-wavelength light source of 193 nm or below, and exhibit improved adhesion to an underlying film or substrate, improved wettability to a developing solution and improved resistance to dry etching. The photosensitive compound includes a carboxylic acid protected with a protective group capable of being deprotected with an acid and has a hydroxy at position No. 3 substituted with a hydrophillic aliphatic compound or a hydrophillic alicyclic compound.

19 Claims, No Drawings

PHOTOSENSITIVE LITHOCHOLATE DERIVATIVE AND CHEMICALLY AMPLIFIED PHOTORESIST COMPOSITION CONTAINING THE SAME

BACKGROUND OF THE INVENTION

1. Field of the Invention

The present invention relates to a photosensitive lithocholate derivative and to a chemically amplified photoresist composition containing the same.

This application is a counterpart of, and claims priority to, Korean Application No. 99-39337, filed Sep. 14, 1999, the contents of which are incorporated herein by reference.

2. Description of the Related Art

As semiconductor devices become highly integrated, photolithography processes used in the fabrication of such devices must be capable of forming ultra-fine patterns. For example, a sub-quarter micron or smaller sized pattern is needed in a semiconductor memory device having a capacity exceeding 1 Gbit. As such, a photolithography technology has beery proposed which employs an argon fluoride (ArF) excimer laser as a new type of light source. This is because the ArF laser exhibits a wavelength (193 nm) which is shorter than the wavelength (248 nm) of a conventional krypton fluoride KrF excimer laser. Therefore, a demand has arisen for chemically amplified photoresist polymers and photoresist compositions which are suitable for use with the ArF excimer laser.

In general, a chemically amplified photoresist composition for an ArF excimer laser should exhibit the following characteristics: (1) transparency at a wavelength of 193 nm; (2) high resistance to dry etching; (3) good adhesion to underlying (and overlying) film materials; and (4) easily capable of being developed using developing solutions which are in widespread use in the manufacture of semiconductor devices.

However, a terpolymer comprising methylmethacrylate, t-butyl methacrylate and methacrylic acid monomers, which is a widely known chemically amplified photoresist polymer for the ArF excimer laser, does not exhibit all of the above-mentioned characteristics. In particular, the terpolymer has a very low resistance to dry etching, and a low adhesion to underlying film materials.

Recently, attempts have been made to increase the etching resistance of a photosensitive polymer for the ArF excimer laser by introducing alicyclic compounds, for example, isobornyl, adamantyl or tricyclodecanyl group, into the backbone of the polymers. However, these polymers also have several disadvantages. For example, their etching resistance is still not acceptable and their adhesion characteristics to underlying films are still poor, which results in lifting of photoresist patterns.

U.S. Pat. No. 5,786,131 discloses mono-, di- ortri-protected hydroxy androstane-17-alkylcarboxylate such as t-butyl-3-acetyllithocholate, t-butyl 3-trifluoroacetyllithocholate or t-butyl lithocholate as an additives for increasing the etching resistance of a resist composition having poor etching resistance. While the lithocholate derivatives disclosed in this patent can be used as an additive for increasing the etching resistance of the resist composition, they cannot by themselves be used as a main component of the resist composition since they are brittle and exhibit poor wettability against a developing solution.

SUMMARY OF THE INVENTION

It is an objective of the present invention to provide a photosensitive compound which maintains transparency even when exposed to a short-wavelength light source of 193 nm or below, and which has improved adhesion to an underlying film or substrate, improved wettability to a developing solution and improved resistance to dry etching.

It is another objective of the present invention to provide a chemically amplified photoresist composition containing the photosensitive compound.

According to one aspect of the present invention, there is provided a photosensitive lithocholate derivative having a carboxylic acid protected with a protective group capable of being deprotected with an acid and having a hydroxy at position No. 3 substituted with a hydrophillic atliphatic compound or a hydrophillic alicyclic compound selected from the group consisting of alken glycol, poly(alken glycol), alken glycol aliphatic hydrocarbon ether and alken glycol alicyclic hydrocarbon ether, poly(alken glycol) aliphatic hydrocarbon ether and poly(alken glycol) alicyclic hydrocarbon ether.

According to another aspect of the present invention, there is provided a chemically amplified photoresist composition including a first photosensitive lithocholate derivative, a second photosensitive lithocholate derivative, or a mixture thereof, and a photoacid generator contained in an amount of 1 to 15% by weight based on the total weight of the photosensitive lithocholate, wherein the first photosensitive lithocholate derivative has a carboxylic acid protected with a protective group capable of being deprotected with an acid and having a hydroxy at position No. 3 substituted with a hydrophillic aliphatic compound or a hydrophillic alicyclic compound selected from the group consisting of alken glycol, poly(alken glycol), alken glycol aliphatic hydrocarbon ether and alken glycol alicyclic hydrocarbon ether, poly(alken glycol) aliphatic hydrocarbon ether and poly(alken glycol) alicyclic hydrocarbon ether, and the second photosensitive lithocholate derivative has a carboxylic acid protected with a protective group capable of being deprotected with anacid and has a hydroxy at position No. 3 substituted with a hydrophillic alicyclic compound selected from the group consisting of alken glycol lithocholic ether, alken glycol lithocholate ether, poly(alken glycol) lithocholic ether and poly(alken glycol) lithocholate ether.

The chemically amplified photoresist composition may further include 0.01 to 2.0% by weight of an organic base based on the total weight of the photosensitive compound.

The photosensitive compound according to the present invention maintains transparency even when exposed to a short-wavelength light source, and exhibits improved adhesion to an underlying film or substrate, improved wettability to a developing solution, and improved resistance to dry etching.

DESCRIPTION OF THE PREFERRED EMBODIMENTS

A photosensitive compound and a chemically amplified photoresist composition containing the same according to the present invention will now be described. Also, a preferred photolithography process using the chemically amplified photoresist composition will also be described. This invention may, however, be embodied in many different forms, and these embodiments are provided so that this disclosure will be thorough and complete, and will fully convey the scope of the invention to those skilled in the art.

Photosensitive Compound

A photosensitive compound according to the present invention is a photosensitive lithocholate derivative having a carboxylic acid protected with a protective group capable of being deprotected with an acid and having a hydroxy at position No. 3 substituted with hydrophillic aliphatic compound or hydrophillic alicyclic compound.

The protective group causes the lithocholate derivative to exhibit insolubility to a developing solution when it is bonded thereto. However, if the protective group is deprotected, that is, decomposed by an acid generated during exposure, a lithocholic acid derivative is generated, thereby exhibiting a greater solubility to a developing solution.

Thus, in consideration of a difference in the solubility of the photosensitive compound before and after exposure, the protective group is preferably t-butyl, 2-methyladamantyl, tetrahydropyranyJ or tetrahyd-rofuranyl.

The photosensitive lithocholate derivative according to a first embodiment of the present invention has a hydroxy at position No. 3 substituted with a hydrophillic aliphatic compound or a hydrophillic alicyclic compound selected from the group consisting of alken glycol, poly(alken glycol), alken glycol aliphatic hydrocarbon ether, alken glycol alicyclic hydrocarbon ether, poly(alken glycol) aliphatic hydrocarbon ether and poly(alken glycol) alicyclic hydrocarbon ether.

Here, the alken glycol is preferably $C_2$ to $C_6$ alken glycol, more preferably ethylene glycol or propylene glycol. The number of alken glycols in poly(alken glycol) is determined in consideration of the molecular weight and polarity of the photosensitive lithocholate derivative. Preferably, poly(alken glycol) consists of 2 to 50 alken glycols.

The aliphatic hydrocarbon and alicyclic hydrocarbon substituted for the hydroxy of alken glycol or poly(alken glycol) to form ether is a $C_1$ to $C_{20}$ hydrocarbon.

The molecular weight and polarity of the photosensitive lithocholate derivative can be adjusted by varying the kind of substituent at position No. 3.

A photosensitive compound according to a first embodiment of the present invention can be represented by the formula (1):

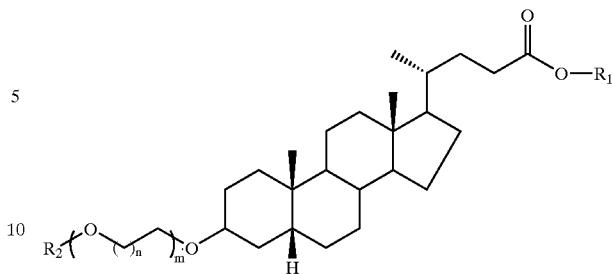

wherein $R_1$ is a protective group, $R_2$ is hydrogen, a $C_1$ to $C_{20}$ aliphatic hydrocarbon or a $C_1$ to $C_{20}$ alicyclic hydrocarbon, n is an integer of 1 to 5, and m is an integer of 1 to 50.

A photosensitive lithocholate derivative according to a second embodiment of the present invention has a hydroxy at a position of No. 3 substituted with a hydrophillic alicyclic compound selected from the group consisting of alken glycol lithocholic acid ether, alken glycol lithocholate ether, poly(alken glycol) lithocholic ether and poly(alken glycol) lithocholate ether.

Here, like in the first embodiment, the alken glycol is preferably $C_2$ to $C_6$ alken glycol, more preferably ethylene glycol or propylene glycol. The poly(alken glycol) consists of 2 to 50 alken glycols.

The lithocholate substituted for the alken glycol or poly(alken glycol) to form the ether compound preferably has a protective group which can be deprotected by an acid or a dissolution inhibitor group substituted for a carboxyl group.

The protective group is preferably t-butyl, 2-methyladamantyl, tetrahydropyranyl or tetrahydrofuranyl.

The dissolution inhibitor group is a hydrophobic group which is not decomposed by an acid generated during exposure, and is introduced for preventing an unexposed region from being developed due to a large amount of hydrophillic functional group, e.g., a carboxyl group, in the photosensitive compound in the case of using a general developing solution. Examples of the dissolution inhibitor group include a $C_1$ to $C_{20}$ aliphatic hydrocarbon or a $C_1$ to $C_{20}$ alicyclic hydrocarbon.

A photosensitive compound according to a second embodiment of the present invention can be represented by the formula (2):

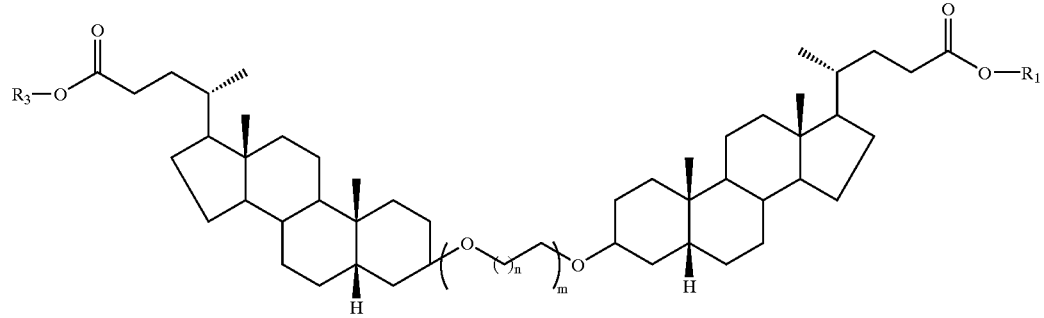

wherein $R_1$ is a protective group, $R_3$ is hydrogen, a protective group or a dissolution inhibitor group, n is an integer of 1 to 5, and m is an integer of 1 to 50.

The photosensitive compound according to the present invention is transparent even when exposed to a short-wavelength light source of 193 nm or below. Also, since the photosensitive compound has an alicyclic structure, the etching resistance thereof is large. Further, since a hydrophillic aliphatic compound or a hydrophillic alicyclic compound is substituted for a hydroxy at position No. 3, the compound exhibits good adhesion to an underlying film or substrate and excellent wettability to a developing solution. Also, the molecular weight and polarity of the photosensitive lithocholate derivative can be easily adjusted by varying the kind of substituent introduced to a hydroxy.

Chemically Amplified Photoresist Composition

A chemically amplified photoresist composition of the present invention includes the above-described photosensitive compound and a photoacid generator.

The photoacid generator is preferably contained in an amount of 1 to 15% by weight based on the total weight of the photosensitive compound.

The photoacid generator is preferably a substance that has a high thermal stability. Therefore, suitable photoacid generators include triarylsulfonium salts, diaryliodonium salts, sulfonates or N-hydroxysuccinimide triflates.

Examples of photoacid generators include triphenylsulfonium triflate, triphenylsulfonium antimonate, diphenyliodonium triflate, diphenyliodonium antimonate, methoxydiphenyliodonium triflate, di-t-butyidiphenyliodonium triflate, 2,6-dinitro benzyl sulfonate or pyrogallol tris(alkylsulfonates), pyrogalloltris(alkylsulfonates)), norbornenedicarboximide triflate, triphenylsulfonium nonaflate, diphenyliodonium nonaflate, methoxydiphenyliodonium nonaflate, di-t-butyl diphenyliodonium nonaflate, N-hydroxysuccinimide nonaflates, norbornene dicarboximide nonaflate, triphenylsulfonium perfluorooctanesulfonates, diphenyliodonium perfluorooctanesulfonates, methoxydiphenyliodonium perfluorooctane sulfonates, di-t-butyidiphenyliodonium triflate, N-hydroxysuccinimide perfluorooctanesulfonates, or norbornene dicarboximide perfluorooctanesulfonates.

Preferably, the chemically amplified photoresist composition of the present invention further includes 0.01 to 2.0% by weight of organic base based on the total weight of the photosensitive compound. Suitable organic bases include triethylamine, triisobutylamine, triisooctylamine, diethanolamine, triethanolamine or a mixture thereof. The organic base is added for preventing a pattern from being deformed due to the acidolysis of photoresist composition forming unexposed regions, after exposure, which results from diffusion of the acid generated at the exposed regions into the unexposed regions.

Also, the chemically amplified photoresist composition according to the present invention preferably further includes 30 to 200 ppm of an organic or base surfactant. The surfactant functions to allow the photoresist composition to be uniformly coated on a substrate.

Method for Preparing Photosensitive Lithocholate

Method for Preparing Photosensitive Lithocholate Derivative According to a First Embodiment Synthesis of Tosylated Hydrophilic Compound A hydrophilic aliphatic compound or a hydrophilic alicyclic compound (I) is reacted with p-toluene sulfonyl chloride (TsCl) (II) to tosylate the same, as expressed by the following reaction scheme (1):

[Reaction scheme 1]

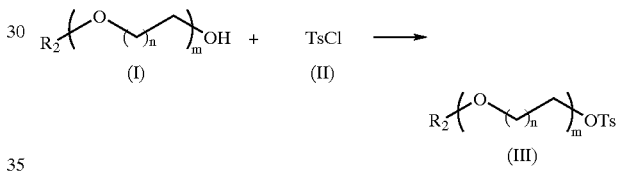

wherein $R_2$ is hydrogen or a $C_1$ to $C_{20}$ aliphatic hydrocarbon group or a $C_1$ to $C_{20}$ alicyclic hydrocarbon group, n is an integer from 1 to 5, and m is an integer from 1 to 50.

Synthesis of Hydrophilic Compound Substituted Lithocholate

A tosylated hydrophilic compound (III) is reacted with a lithocholate (IV) as expressed by the following reaction scheme (2):

[Reaction scheme (2)]

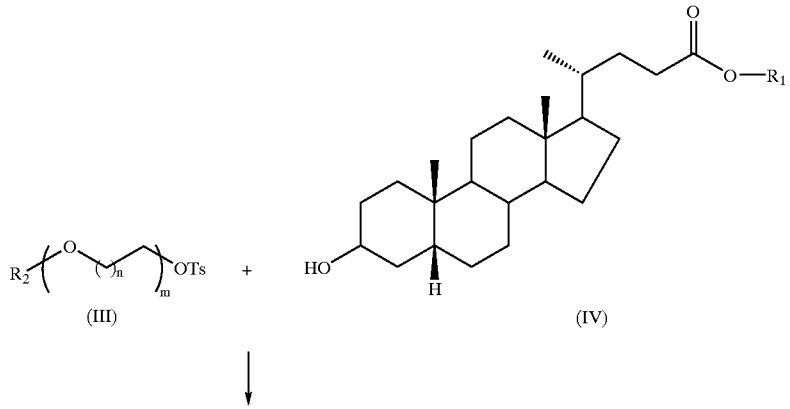

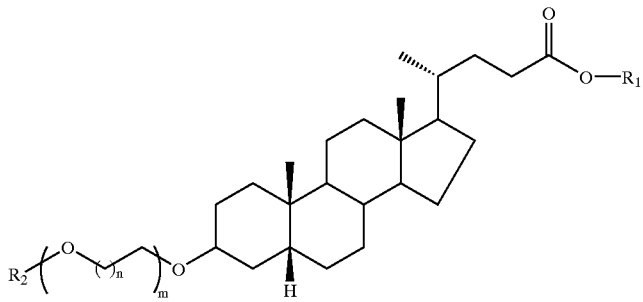

wherein $R_1$ is a protective group. Then, a hydrophilic compound substituted lithocholate is formed by $S_N2$ reaction.

Method for Preparing Photosensitive Lithocholate Derivative According to a Second Embodiment Synthesis of Tosylated Hydrophilic Compound Alken glycol or poly(alken glycol) (V) is reacted with TsCl (II) to prepare a compound (VI) having two hydroxy groups tosylated, as expressed by the following reaction scheme (3):

[Reaction scheme 3]

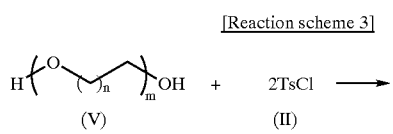

Synthesis of Hydrophilic Alicyclic Compound Substituted Lithocholate

Tosylated alken glycol or tosylated poly(alken glycol) (VI) is reacted with first lithocholate (VII) and second lithocholate (VIII) to prepare hydrophilic alicyclic compound substituted lithocholate by $S_N2$ reaction, as expressed by the following reaction scheme (4):

[Reaction scheme (4)]

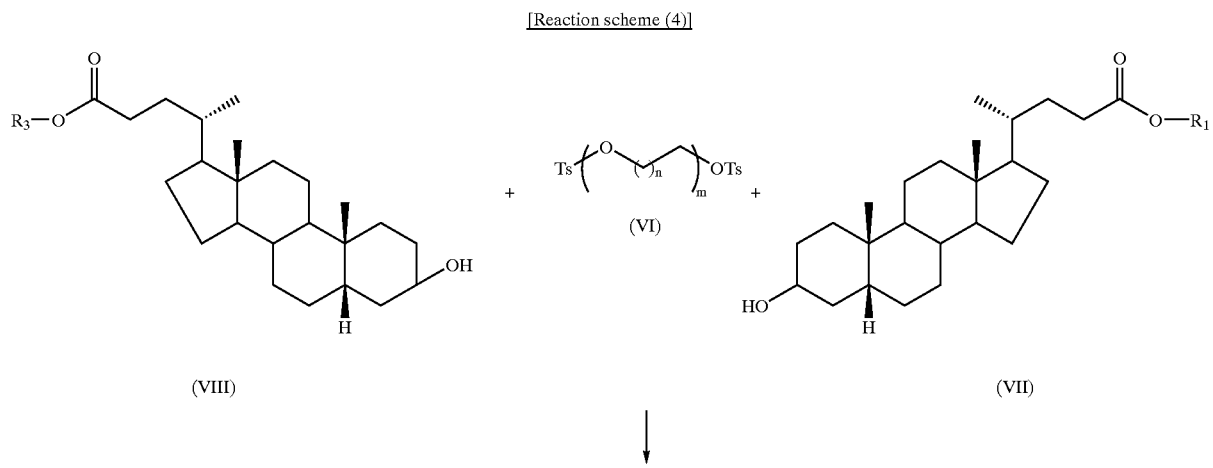

-continued

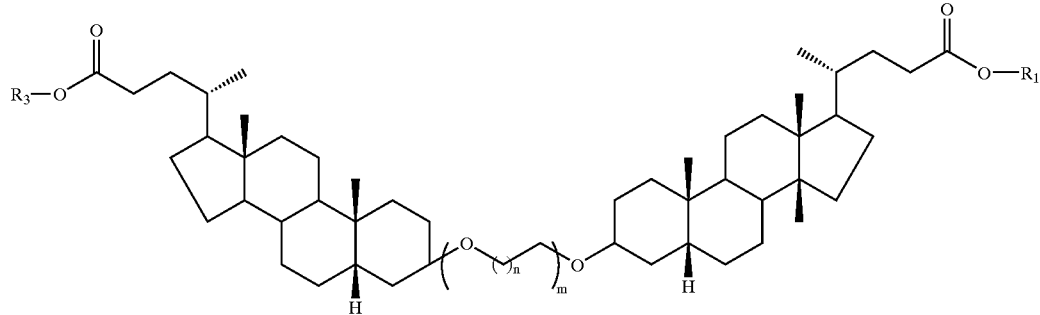

wherein $R_1$ is a protective group, $R_3$ is hydrogen, a protective group or a dissolution inhibitor group, n is an integer from 1 to 5, and m is an integer from 1 to 50. Then, a hydrophilic compound substituted lithocholate is formed by $S_N2$ reaction.

Method of Preparing Chemically Amplified Photoresist Composition and Photolithography Process Using the Same The chemically amplified photoresist composition according to the present invention is prepared by dissolving the photosensitive compound prepared in the above-described manner and a photoacid generator, in an appropriate solvent, for example, propylene glycol monomethyl ether acetate (PGMEA), and mixing the same. Here, the photoacid generator is mixed in an amount of 1 to 15% by weight based on the weight of the polymer. Also, it is preferable to complete the photoresist composition by further dissolving 0.01 to 2.0% by weight of an organic base based on the weight of the polymer. Also, 30 to 200 ppm of a surfactant is preferably further included in the composition.

The chemically amplified photoresist composition prepared in the above-described manner can be used for a general photolithography process, and is particularly suitable for forming a fine pattern which satisfies a design rule of 0.20 μm or smaller using an ArF excimer laser as an exposure light source.

First, the photoresist composition is coated on a substrate where a patterning object material layer is formed, to form a photoresist layer having a predetermined thickness, preferably 0.2 to 2 μm. Subsequently, pre-baking is carried out on the photoresist layer. The pre-baking step is performed at a temperature of 70 to 160° C. for 30 to 360 seconds. After the pre-baking step, the photoresist layer is exposed using a mask having a predetermined pattern, using an exposure light source having a wavelength of 248 nm or less, preferably an ArF excimer laser having a wavelength of 193 nm. Acid is generated from the photoacid generator contained in the photoresist layer by exposure. The photosensitive compound is acidolyzed by the catalytic action of the thus-generated acid to form a lot of carboxy groups, as expressed by reaction scheme 5. As a result, a large amount of hydrophilic groups, e.g., carboxy groups, are produced in the exposed region of the photoresist layer. Thus, a noticeable difference in the polarity of the photoresist layer is created between an exposed region and an unexposed region. That is, contrast is noticeably increased.

[Reaction scheme 5]

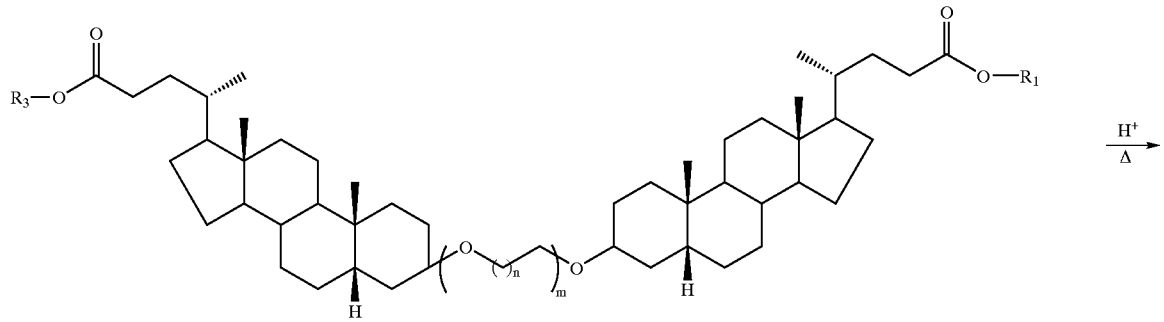

-continued

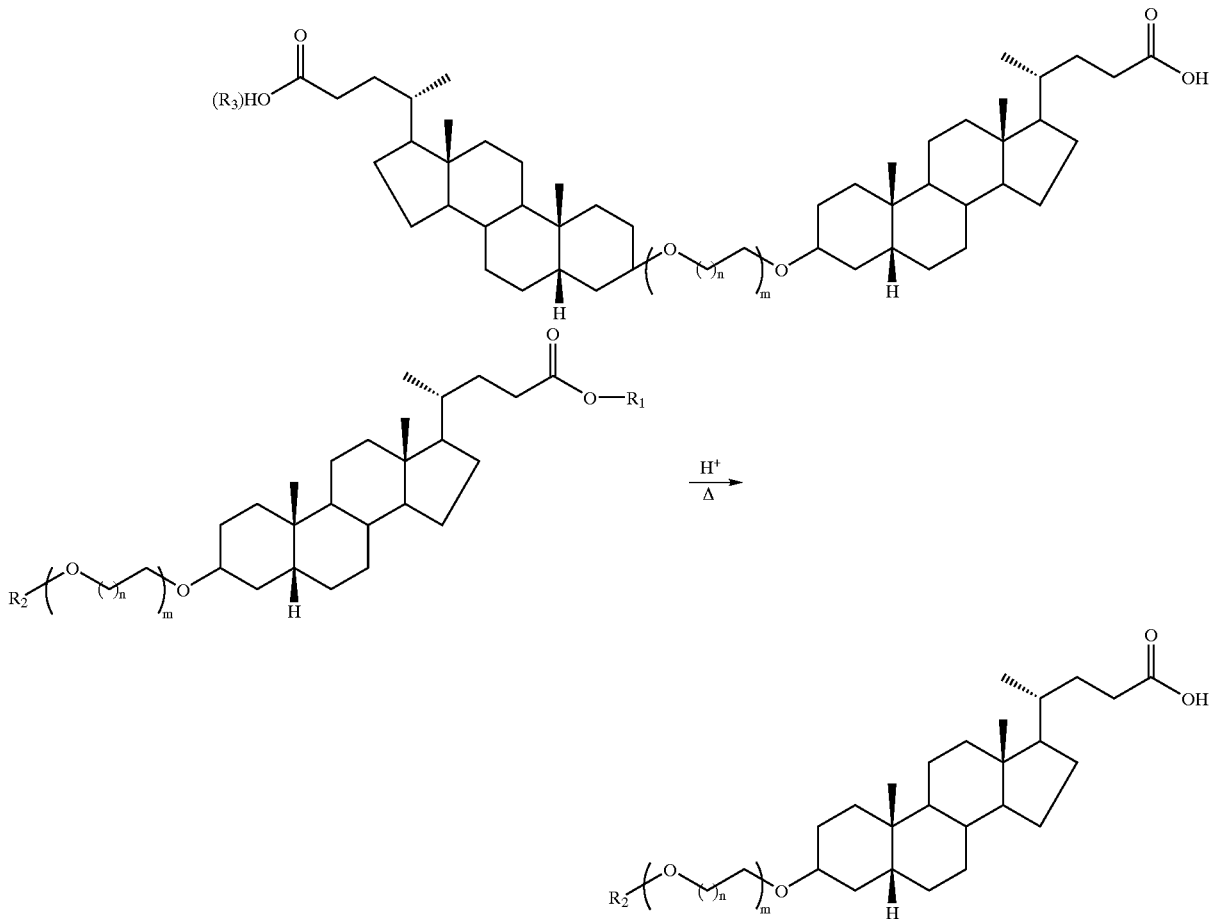

The parentheses enclosing $R_3$ denote that $R_3$ is not acidolyzed but is retained since it is a dissolution inhibitor group.

After exposure, the photoresist layer is thermally treated for a short time before development, which is referred to as a post-exposure-thermal treatment. The post-exposure-thermal treatment is performed for the purpose of increasing contrast by further activating acidolysis of exposed regions by the acidic catalyst, that is, for the purpose of increasing contrast by acidolyzing a protective group contained in the photosensitive compound in the exposed region.

Next, development is performed using an appropriate developing solution to complete a photoresist pattern. Here, the developing solution used is a developing solution for general development processes, for example, 2.38% by weight of tetramethylammonium hydroxide (TMAH). Since the photosensitive compound according to the present invention has a polarity, it exhibits excellent wettability against a developing solution. Thus, development is facilitated by using the conventional developing solution.

After forming the photoresist pattern, a patterning object layer is etched to form a desired pattern. The photoresist pattern of the present invention is formed of a photoresist compound having several alicyclic structures, and thus the etching resistance thereof is large. Therefore, a pattern having a good profile, that is, having a precise critical dimension, can be formed.

While not being limited thereto, the present invention will now be described in more detail with reference to the following examples.

Synthesis of Tosylated Ether

EXAMPLE 1

12 g of di(ethylene glycol) methyl ether (0.1 mol) was put in a round-bottom flask and completely dissolved using methylene chloride, and then 11 g of triethylamine (0.11 mol) was added thereto. 23 g of TsCl (0.12 mol) was slowly dropped to the resultant solution at room temperature. The reaction was identified by thin layer chromatography and then reactants were washed several times using an aqueous sodium carbonate solution to obtain tosylated di(ethylene glycol)methyl ether.

EXAMPLE 2

The same conditions as Example 1 were applied, except that, instead of di(ethylene glycol) methyl ether, 13.4 g of di(ethylene glycol) ethyl ether (0.1 mol), 16.2 g of di(ethylene glycol) butyl ether (0.1 mol), 19 g of di(ethylene glycol) hexyl ether (0.1 mol), 27.4 g of di(ethylene glycol) dodecyl ether (0.1 mol), 27.2 g of di(ethylene glycol) 2-ethyl hexyl ether (0.1 mol), 16.4 g of tri(ethylene glycol) methyl ether (0.1 mol), 17.8 g of tri(ethylene glycol) ethyl ether (0.1 mol), 14.8 g of di(propylene glycol) methyl ether (0.1 mol), 17.6 g of di(propylene glycol) propyl ether (0.1 mol), 19 g of di(propylene glycol) butyl ether (0.1 mol), 19 g of di(propylene glycol) t-butyl ether (0.1 mol), 20.6 g of tri(propylene glycol) methyl ether (0.1 mol), 23.4 g of tri(propylene glycol) propyl ether (0.1 mol), 20.6 g of tri(propylene glycol) butyl ether (0.1 mol), 0.1 mol of poly(ethylene glycol) methyl ether having an average-number molecular weight of 200 to 10000, 0.1 mol of poly(ethylene glycol) butyl ether having an average-number molecular weight of 200 to 10000, and 0.1 mol of poly (propylene glycol) butyl ether having an average-number molecular weight of 300 to 10000, were used to obtain tosylated di(ethylene glycol) ethyl ether, tosylated di(ethylene glycol) butyl ether, tosylated di(ethylene glycol) hexyl ether, tosylated di(ethylene glycol) dodecyl ether, tosylated di(ethylene glycol) 2-ethyl hexyl ether, tosylated tri(ethylene glycol) methyl ether, tosylated tri(ethylene glycol) ethyl ether, tosylated di(propylene glycol) methyl ether, tosylated di(propylene glycol) propyl ether, tosylated di(propylene glycol) butyl ether, tosylated di(propylene glycol) t-butyl ether, tosylated tri(propylene glycol) methyl ether, tosylated tri(propylene glycol) propyl ether, tosylated tri(propylene glycol) butyl ether, tosylated poly(ethylene glycol) methyl ether, tosylated poly(ethylene glycol) butyl ether, and tosylated poly(propylene glycol) butyl ether, respectively.

EXAMPLE 3

The same conditions as in Example 1 were used, except that each 1 mol of ethylene glycol, di(ethylene glycol), tri(ethylene glycol), poly(ethylene glycol), propylene glycol, di(propylene glycol), tri(propylene glycol) or poly (propylene glycol) having an average-number molecular weight of 400 to 50000, instead of di(ethylene glycol) methyl ether, and 46 g of TsCI (0.24 mol) were used, to tosylate two hydroxy groups positioned at both ends of the glycols.

Synthesis of Photosensitive Lithocholate Derivative

EXAMPLE 4

1.1 equivalent of sodium hydride with respect to t-butyl lithocholate to be used, was put into a round-bottom flask, THF was added thereto and then stirred. The mixed solution was cooled to 0° C. and then t-butyl lithocholate was put into the mixed solution. T-butyl lithocholate was prepared by a method known and described in J. Chem. Soc. Perkin trans. I., 2245 (1990). The t-butyl lithocholate added solution was stirred for about 10 minutes and the temperature of the solution was raised to room temperature. Next, tosylated di(ethylene glycol) methyl ether prepared in Example 1 was slowly added to the solution. While identifying the reaction by thin layer chromatography, the resultant was reacted at 60° C. for several hours. After identifying that the reaction was carried out to a considerable extent, the reactant was slowly dropped into petroleum ether to be precipitated, thereby separating an initial product. The initial product was filtered and then dried in a vacuum state, to obtain a pure product, that is, di(ethylene glycol) methyl ether substituted t-butyl lithocholate (yield: 95%)

EXAMPLE 5

The same conditions as Example 4 were applied, except that, instead of tosylated di(ethylene glycol) methyl ether, tosylated ethers prepared in Example 2 were used, to obtain di(ethylene glycol) ethyl ether substituted t-butyl lithocholate (yield: 93%), di(ethylene glycol) butyl ether substituted t-butyl lithocholate (yield: 97%), di(ethylene glycol) hexyl ether substituted t-butyl lithocholate (yield: 95%), di(ethylene glycol) dodecyl ether substituted t-butyl lithocholate (yield: 97%), di(ethylene glycol) 2-ethyl hexyl ether substituted t-butyl lithocholate (yield: 97%), tri(ethylene glycol) methyl ether substituted t-butyl lithocholate (yield: 97%), tri(ethylene glycol) ethyl ether substituted t-butyl lithocholate (yield: 95%), di(propylene glycol) methyl ether substituted t-butyl lithocholate (yield: 95%), di(propylene glycol) propyl ether substituted t-butyl lithocholate (yield: 95%), di(propylene glycol) butyl ether substituted t-butyl lithocholate (yield: 95%), di(propylene glycol) t-butyl ether substituted t-butyl lithocholate (yield: 93%), tri(propylene glycol) methyl ether substituted t-butyl lithocholate (yield: 93%), tri(propylene glycol) propyl ether substituted t-butyl lithocholate (yield: 93%), tri(propylene glycol) butyl ether substituted t-butyl lithocholate (yield: 93%), poly(ethylene glycol) methyl ether substituted t-butyl lithocholate (yield: 90%), poly(ethylene glycol) butyl ether substituted t-butyl lithocholate (yield: 90%), and poly(propylene glycol) butyl ether substituted t-butyl lithocholate (yield: 93%), respectively.

EXAMPLE 6

The same conditions as Example 4 were applied, except that, instead of di(ethylene glycol) methyl ether having only one tosylated hydroxy group, compounds having both hydroxy groups tosylated, prepared in Example 3 were used, to obtain (ethylene glycol) di(t-butyl lithocholic) ether (yield: 90%), di(ethylene glycol) di(t-butyl lithocholic) ether (yield: 90%), tri(ethylene glycol) di(t-butyl lithocholic) ether (yield: 90%), poly(ethylene glycol) di(t-butyl lithocholic) ether (yield: 90%), (propylene glycol) di(t-butyl lithocholic) ether (yield: 92%), di(propylene glycol) di(t-butyl lithocholic) ether (yield: 92%), tri(propylene glycol) di(t-butyl lithocholic) ether (yield: 92%), and poly (propylene glycol) di(t-butyl lithocholic) ether (yield: 92%), respectively.

EXAMPLE 7

In the same manner as Example 4, except that methoxy ethoxy methyl chloride was used instead of tosylated di(ethylene glycol) methyl ether prepared in Example 1, methoxy ethoxy methyl substituted t-butyl lithocholate was obtained (yield: 93%).

Method of Preparing Photoresist Composition and Photolithography Process Using the Same

EXAMPLE 8

1.0 g of a photosensitive compound prepared in Example 4, that is, di(ethylene glycol) methyl ether substituted t-butyl lithocholate, 0.02 g of triphenylsulfornium triflate as a photoacid generator and 2 mg of triisobutylamine as an organic base were dissolved in 8 g of PGMEA. Subsequently, the mixture was filtered using a 0.2 μm filter, resulting in a photoresist composition.

Hexamethyldisilazane was applied to a wafer having an object material layer to be patterned and then the obtained photoresist composition was coated to a thickness of about 0.4 μm. The photoresist composition coated wafer was pre-baked at a temperature of about 140° C. for about 90 seconds, exposed using a mask defining a predetermined pattern and an ArF excimer laser (NA: 0.6) as an exposure light source, and post-baked at a temperature of about 110° C. for about 90 seconds. Thereafter, the resultant was developed using 2.38% by weight of TMAH for about 60 seconds, thereby forming a photoresist pattern.

As a result, a 0.20 μm line and space photoresist pattern was obtained at an exposure dose of about 10 mJ/cm$^2$.

EXAMPLE 9

A photoresist composition was prepared in the same manner as in Example 8 using lithocholate derivatives prepared in Examples 5 through 7, and then a photolithography process was performed.

As a result, 0.13 to 0.20 μm line and space photoresist patterns were obtained at exposure doses of about 5 to 50 mJ/cm$^2$.

EXAMPLE 10

A photoresist composition was prepared in the same manner as in Example 8, except that 0.02 g of triphenylsulfonium nonaflate was used as a photoacid generator instead of triphenylsulfonium triflate, and then a photolithography process was performed. As photosensitive compounds, lithocholate derivatives prepared in Examples 4 through 7 were used.

As a result, a 0.13 to 0.20 μm line and space photoresist pattern were obtained at exposure doses of about 3 to 50 mJ/cm$^2$.

The photosensitive lithocholate derivative according to the present invention has a backbone having several alicyclic groups, and includes a carboxyl group protected by a protective group capable of being deprotected with acid. Also, the photosensitive lithocholate derivative has a hydroxy group at a position of No. 3 alkylated with hydrophilic aliphatic compound or hydrophilic alicyclic compound. Thus, the photosensitive compound according to the present invention maintains transparency even when exposed to a short-wavelength light source, has excellent adhesion to an underlying film or substrate and excellent resistance to dry etching. Further, the molecular weight and polarity of the photosensitive lithocholate derivative can be optionally adjusted by varying substitutes introduced into the hydroxy group.

What is claimed is:

1. A photosensitive lithocholate derivative having a carboxylic acid protected with a protective group capable of being deprotected with an acid and having a hydroxyl at position No. 3 substituted with a hydrophilic aliphatic compound or a hydrophilic alicyclic compound selected from the group consisting of poly(alken glycol) consisting of 2 to 50 alken glycols, alken glycol $C_1$ to $C_{20}$ aliphatic hydrocarbon ether, alken glycol $C_1$ to $C_{20}$ alicyclic hydrocarbon ether, poly(alken glycol) aliphatic $C_1$ to $C_{20}$ hydrocarbon ether consisting of 2 to 50 alken glycols, and poly(alken glycol) alicyclic $C_1$ to $C_{20}$ hydrocarbon ether consisting of 2 to 50 alken glycols.

2. A photosensitive lithocholate derivative having a carboxylic acid protected with a protective group capable of being deprotected with an acid and having a hydroxy at position No. 3 substituted with a hydrophillic alicyclic compound selected from the group consisting of alken glycol lithocholic ether, alken glycol lithocholate ether, poly(alken glycol) lithocholic ether and poly(alken glycol) lithocholate ether.

3. The photosensitive lithocholate derivative according to claim 2, wherein the alken glycol is $C_2$ to $C_6$ alken glycol.

4. The photosensitive lithocholate derivative according to claim 3, wherein the alken glycol is ethylene glycol or propylene glycol.

5. The photosensitive lithocholate derivative according to claim 2, wherein the poly(alken glycol) consists of 2 to 50 alken glycols.

6. The photosensitive lithocholate derivative according to claim 2, wherein the protective group is t-butyl, 2-methyladamantyl, tetrahydropyranyl or tetrahydrofuranyl.

7. The photosensitive lithocholate derivative according to claim 2, wherein the lithocholate for forming an ether by being substituted with the alken glycol or poly(alken glycol) has a protective group capable of being deprotected with an acid or a dissolution inhibitor group as a substituent.

8. The photosensitive lithocholate derivative according to claim 7, wherein the protective group is t-butyl, 2-methyladamantyl, tetrahydropyranyl or tetrahydrofuranyl, and the dissolution inhibitor group is a $C_1$ to $C_{20}$ aliphatic hydrocarbon or $C_1$ to $C_{20}$ alicyclic hydrocarbon.

9. A chemically amplified photoresist composition comprising:
   a first photosensitive lithocholate derivative, a second photosensitive lithocholate derivative, or a mixture thereof; and
   a photoacid generator contained in an amount of 1 to 15% by weight based on the total weight of the photosensitive lithocholate derivative
   wherein the first photosensitive lithocholate derivative has a carboxylic acid protected with a protective group capable of being deprotected with an acid and having a hydroxy at position No. 3 substituted with a hydrophillic aliphatic compound or a hydrophillic alicyclic compound selected from the group consisting of alken glycol, poly(alken glycol), alken glycol aliphatic hydrocarbon ether and alken glycol alicyclic hydrocarbon ether, poly(alken glycol) aliphatic hydrocarbon ether and poly(alken glycol) alicyclic hydrocarbon ether, and
   the second photosensitive lithocholate derivative has a carboxylic acid protected with a protective group capable of being deprotected with an acid and has a hydroxy at position No. 3 substituted with a hydrophillic alicyclic compound selected from the group consisting of alken glycol lithocholic ether, alken glycol lithocholate ether, poly(alken glycol) lithocholic ether and poly(alken glycol) lithocholate ether.

10. The chemically amplified photoresist composition according to claim 9, wherein the photoacid generator is a triarylsulfonium salt, a diaryliodonium salt, a sulfonate, a N-hydroxysuccinimide triflate or a mixture thereof.

11. The chemically amplified photoresist composition according to claim 9, further comprising 0.01 to 2.0% by weight of an organic base based on the total weight of the photosensitive lithocholate derivative.

12. The chemically amplified photoresist composition according to claim 11, wherein the organic base is triethylamine, triisobutylamine, trioctylamine, diethanolamine, triethanolamine, or a mixture thereof.

13. The chemically amplified photoresist composition according to claim 9, wherein the alken glycol is $C_2$ to $C_6$ alken glycol.

14. The chemically amplified photoresist composition according to claim 9, wherein the poly(alken glycol) consists of 2 to 50 alken glycols.

15. The chemically amplified photoresist composition according to claim 9, wherein the aliphatic hydrocarbon or alicyclic hydrocarbon is a $C_1$ to $C_{20}$ hydrocarbon.

16. The chemically amplified photoresist composition according to claim 9, wherein the protective group is t-butyl, 2-methyladamantyl, tetrahydropyranyl or tetrahydrofuranyl.

17. The chemically amplified photoresist composition according to claim 9, wherein the lithocholate for forming an ether by being substituted with the alken glycol or poly (alken glycol) has a protective group capable of being deprotected with an acid or a dissolution inhibitor group as a substituent.

18. The chemically amplified photoresist composition according to claim 17, wherein the protective group is t-butyl, 2-methyladamantyl, tetrahydropyranyl or tetrahydrofuranyl.

19. The chemically amplified phtoresist composition according to claim 17, wherein the dissolution inhibitor group is a $C_1$ to $C_{20}$ aliphatic hydrocarbon or $C_1$ to $C_{20}$ alicyclic hydrocarbon.

\* \* \* \* \*